United States Patent [19]

Brookfield

[11] 4,175,425
[45] Nov. 27, 1979

[54] VISCOMETER

[76] Inventor: David A. Brookfield, 168 Massapoag Ave., Sharon, Mass. 02067

[21] Appl. No.: 917,470

[22] Filed: Jun. 21, 1978

Related U.S. Application Data

[63] Continuation-in-part of Ser. No. 786,015, Apr. 8, 1977, abandoned.

[51] Int. Cl.² ............................................. G01N 11/14
[52] U.S. Cl. ......................................................... 73/59
[58] Field of Search ....................................... 73/59, 60

[56] References Cited

U.S. PATENT DOCUMENTS

| | | | |
|---|---|---|---|
| 2,519,378 | 8/1950 | Kilpatrick | 73/59 |
| 2,817,231 | 12/1957 | Barstow | 73/60 |
| 3,122,914 | 3/1964 | Stabe et al. | 73/59 |
| 3,349,606 | 10/1967 | Merrill et al. | 73/60 |
| 3,435,666 | 4/1969 | Fann | 73/59 X |
| 3,986,388 | 10/1976 | Stolzy | 73/59 |

Primary Examiner—Charles A. Ruehl
Assistant Examiner—Joseph W. Roskos

[57] ABSTRACT

A viscometer of the type has a chamber within which there are concentric, open ended cylindrical elements, one within the other. A drive is provided to rotate one of the elements and the inner element, which is free to turn, has one end of a readout rod connected axially thereto. The readout rod extends freely through a tube which seals the rod against the fluid flowing through the chamber and its other end is outside the viscometer with the rotor of a readout device connected thereto. The major percentage of the wanted torsional resistance against the turning of the inner element relative to the other element is provided by a resilient device which also ensures lateral stability for the inner element thus enabling the rod-sealing tube to offer but a minor percentage of such resistance. The readout rod is held by a bearing adjacent its outer end and close to the center of gravity of the rotor.

11 Claims, 6 Drawing Figures

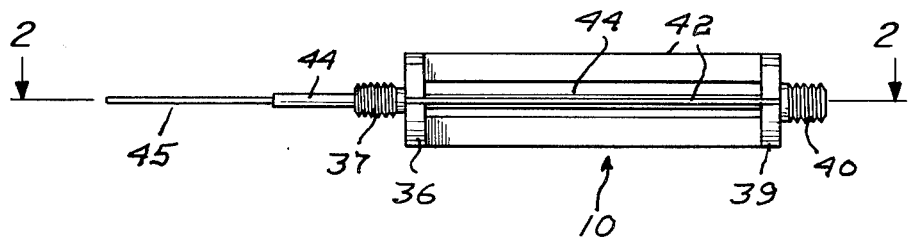
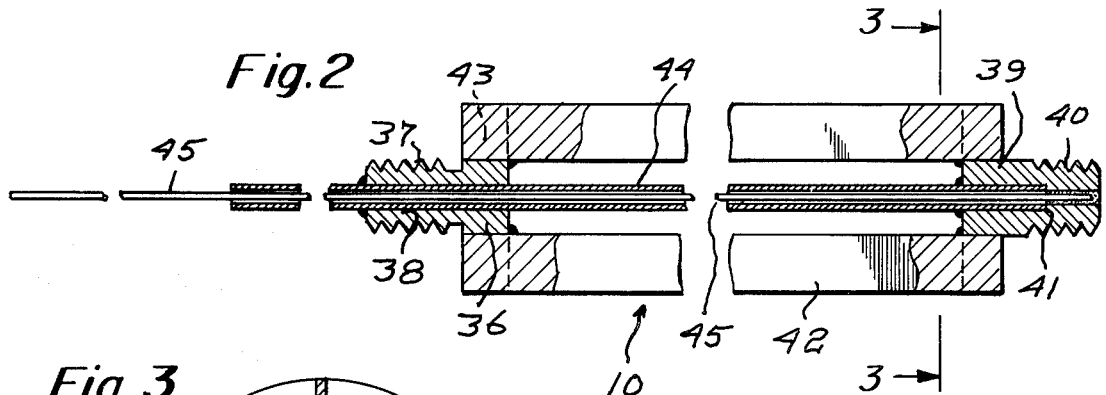
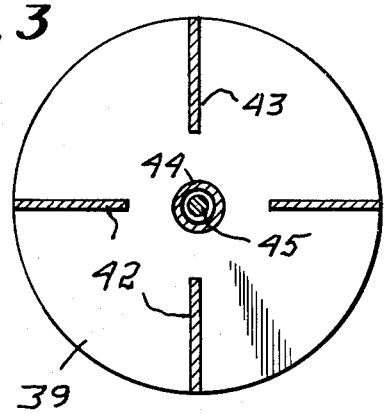
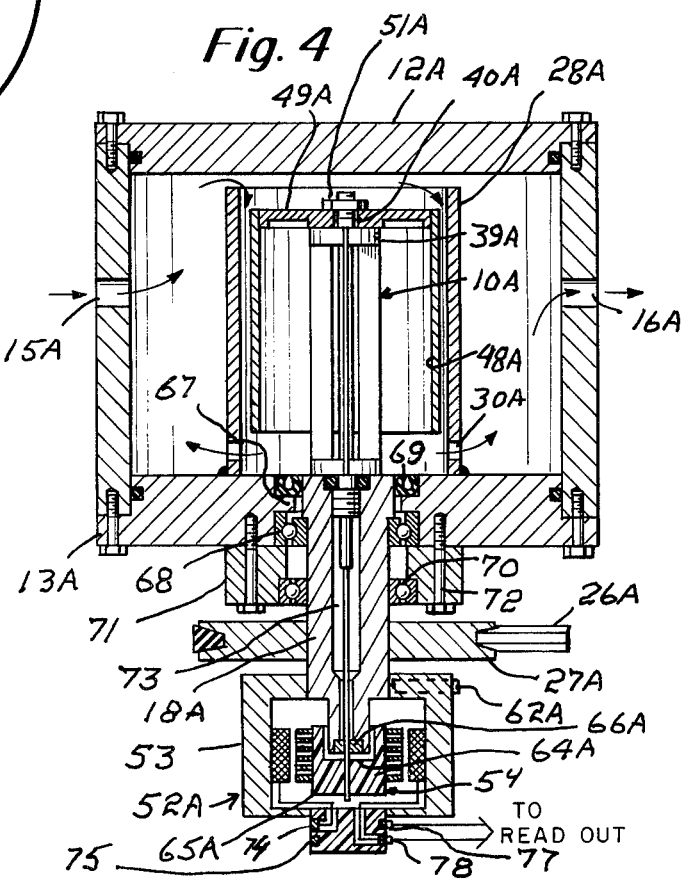

VISCOMETER

The present invention is a continuation-in-part of Ser. No. 786,015, filed April 8, 1977 and now abandoned.

BACKGROUND REFERENCES

U.S. Pat. No. 2,821,860
U.S. Pat. No. 2,817,231
U. S. Pat. No. 2,519,378

BACKGROUND OF THE INVENTION

One type of viscometer particularly well illustrates the problem with which the present invention is concerned and which is common to other viscometers where lateral deflection of the part that is free to turn would adversely affect accuracy.

That type of viscometer has open ended cylinders within the liquid the viscosity of which is to be monitored, one cylinder with the inner cylinder driven by the medium in the space between them in response to the turning of the driving cylinder. Such a viscometer requires a torsion unit within the medium in support of the driven cylinder and such includes a first fixed part and a second connected axially to the driven cylinder. A readout element extends freely through a metal tube that is the axial support of the second part and has its ends sealed to both parts. The readout element has one end axially anchored to turn with the driven cylinder and has its other end operatively connected outside the medium to readout means providing wanted information as the driven cylinder is turned by the medium between it and the driving cylinder. The above type of viscometer well illustrates the necessity of ensuring lateral stability as well as torsional resistance.

The metal tube presents the problem with torsion devices having readout means responsive to the turning of a part, on the application of torque thereto above a predetermined value, when lateral deflection of said part, the readout element or both would be the cause of inaccurate readout information. The metal tube, while necessary to protect and seal the readout element from the liquid, also had to provide both the lateral stability for the driven cylinder and torsional resistance against its turning. As a consequence, the tubes, prior to the present invention, have been of a relatively large diameter and thick walled stock and hence of such stiffness that the sensitivity of such torsion devices has been seriously limited.

THE PRESENT INVENTION

The general objective of the present invention is to provide viscometers which are free of the restrictions imposed by prior constructions. In accordance with the invention, this objective is attained with each viscometer having a housing providing a chamber through which fluid under pressure flows and within which there are first and second, concentric, open ended cylindrical elements, one within the other with a clearance appropriate for the flow of liquid between them. Means are provided to rotate one element relative to the others with such means having a shaft extending into the chamber and connected axially to the element to be rotated. Either the shaft or a wall of the housing has a threaded port extending therethrough and coaxial with the elements. Coaxial torque responsive means are provided to support the inner element and prevent its contact with the other element with such means provided with a hub threaded in the port and having an axial passage extending therethrough, a part, which may also be a hub, connected axially to the inner element and means connecting that part to the hub to enable that part to turn relative thereto.

The connecting means include a tube sealed axially to the part connected to the inner element and to the hub and resilient means arranged about the tube and connected to the hub and that part and operable to provide both lateral stability for the inner element and the major percentage of the wanted torsional resistance to the turning thereof. A readout rod extends freely through the tube with its inner end anchored to turn with the inner element and its outer end exposed externally of the viscometer housing. The inside diameter of the tube is such that the readout rod is a free but close fit therein and the outside diameter of the tube is such that the tube provides a minor percentage of the wanted torsional resistance but establishes a wall that is not deformable against the readout rod by the fluid pressure within the chamber which may be as high as 500 P.S.1 but is more commonly in the 100 to 150 PSI range.

A readout device, a magnetic transducer, has its rotor fixed on the exposed end of the readout rod and an important objective of the invention is to ensure that the rotor is not deflected when the viscometer is in use, an objective attained with a support to which the coil containing part of the transducer is secured and which has a passage through which the readout rod freely extends. The outer end of the support has a bearing through which the readout rod extends and which is located close to the center of gravity of the rotor thus ensuring the accuracy of the readout by preventing lateral movement of the rotor.

BRIEF DESCRIPTION OF THE DRAWINGS

In the accompanying drawings, preferred embodiments of the invention are illustrated and FIG. 1 is a side view of a torsion unit in accordance with one embodiment of the invention;

FIG. 2 is a section, on an increase in scale, taken approximately along the indicated line 2—2 of FIG. 1;

FIG. 3 is a section, on a further increase in scale, taken approximately along the indicated line 3—3 of FIG. 2;

FIG. 4 is a section taken vertically through a viscometer in which the readout rod of the torsion unit extends axially through the shaft by which the drive cylinder is rotated;

THE PREFERRED EMBODIMENTS OF THE INVENTION

Figure 5:
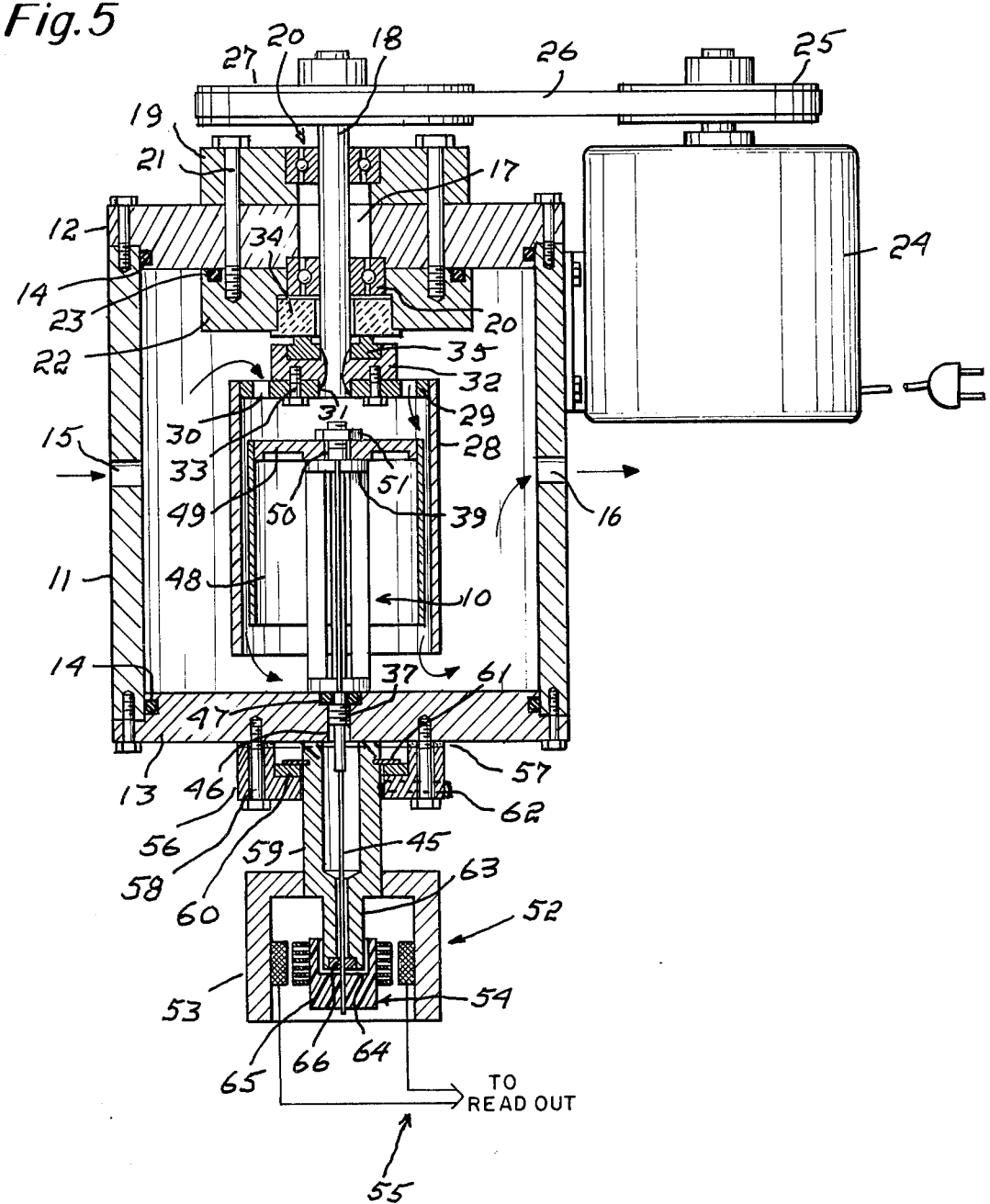
FIG. 5 is a like section through a viscometer in which the drive shaft and the readout rod extend through opposite ends of the viscometer housing.

Reference is first made to FIG. 5 which illustrates a viscometer incorporating a torsion unit in accordance with the invention. The viscometer is of the type previously generally described and the torsion unit is generally indicated at 10 and is shown by itself in FIGS. 1–3.

The viscometer housing consists of a cylindrical side wall 11 and shouldered end walls 12 and 13 fitted and secured thereto and carrying seals 14. The side wall 11 has diametrically opposed inlet and outlet ports 15 and 16, respectively, enabling the viscometer to be placed in a conduit, not shown, for a fluid the viscosity of which is to be monitored.

The end wall 12 has a port 17 freely receiving a shaft 18. An end cap 19 provided with a shaft-supporting ball bearing unit 20 is secured to the end wall 12 by screws 21. A ring 22, within the housing and provided with a seal 23, is also secured by the screws 21. The end wall 12 and the ring 22 carry a second shaft-supporting, ball bearing unit 20. A motor 24 mounted on the side wall 11 has a pulley 25 on its drive shaft with a belt 26 trained about it and a pulley 27 fast on the outer end of the shaft 18.

A first or drive cylinder 28, open at one end, has its end wall 29 provided with inlet ports 30 and an axial port 31 in which the end of the shaft 18 is fitted and is secured to the shaft flange 32 by screws 33. A shaft seal includes a static portion 34 carried by the ring 22 engaged by the annular seal 35 carried by the flange 32.

The torsion unit 10, best seen in FIGS. 1-3, includes a first part 36 provided with a threaded shank 37 and having an axial passage 38 and a second part 39 having a threaded shank 40 and a counterbored axial passage 41 extending therethrough. The two parts 36 and 39 are shown as interconnected by four resilient metal strips 42 having their ends anchored in radial slots 43 spaced 90° apart.

A tube 44, in the disclosed embodiment a metal tube, has its inner end within the counterbore of the passage 41 and is sealed as by welding it to the part 39. The outer end of the tube 44 extends through the passage 38 and is sealed as by welding it to the outer end of the shank 37. The readout rod 45, of small diameter and a free fit within the tube 44 has one end soldered in and closing the passage 41 and its other end extending beyond the outer end of the tube 40 and outside the housing.

The end wall 13 has a port 46 into which the shank 37 of the first part 36 is threaded and a seat at its inner end for a seal 47.

A second cylinder 48, a driven cylinder, open at one end, is a close but free fit within the drive cylinder 28 providing an annular clearance in the approximate range of one-thirty-second to one-half inch, by way of example and not of limitation, a one-eighth inch clearance being the most common. The end wall 49 of the cylinder 48 is provided with an axial port 50 which the shank 40 of the second part fits and the end wall 49 is secured to the second part 39 by a nut 51 threaded on the exposed threaded end of the shank 40.

With the viscometer in use and the motor 24 in operation the liquid flowing between the two cylinders exerts a rotative force on the drive cylinder 48 that increases with the viscosity of the liquid. This force is opposed to a predetermined extent by the torsion unit 10 which also must have such lateral stability as to maintain at all times the driven cylinder 48 concentric with the drive cylinder 28. It will be appreciated that the radially disposed strips 42 ensure lateral stability while their thickness is such that they are resiliently flexible and thus provide torsional resistance.

It will also be appreciated that the dimensions of the tube 44 are important. While the tube 44 is sealed to both of the parts 36 and 39 and hence contributes towards the torsional resistance of the unit 10, its small size enables it to be relatively thin walled and still not collapsed against the readout element 45 as the fluid pressure to which it is subjected may be as high, for example, as 500 PSI with the usual pressure range in the approximate range of 100-150 PSI.

The readout means to which the readout rod 45 is operatively connected may be of any type, in the disclosed embodiments, a magnetic transducer generally indicated at 52, and for convenience, shown schematically as containing a coil holding part 53 surrounding a rotor 54 fast on the outer end of the readout rod 45. The coil circuit is indicated at 55.

Because the diameter of the readout rod is or close to 0.062 inches, it is relatively flexible and to prevent that characteristic from being a cause of inaccurate readout information, it is necessary to ensure lateral stability of the rotor 54. To that end, a ring 56 and a seal 57 are secured to the outer surface of the end wall 13 by screws 58. A hollow post 59 is a close fit in the ring 56 and it and a spring washer 60 are held in place by a retainer 61, thus seating the post 59 against the wall 13 while permitting it to be turned when the set screw 62 is released.

The outer end 63 of the post 59 is of reduced diameter and extends into the recess 64 in the magnet holder 65 of the rotor 54. The coil holding part 53 is secured to the post 59 adjacent the shoulder defined by said outer end 63. The readout rod 45 is held by a bearing 66 at the outer end of the passage through the post and is substantially at the center of gravity of the rotor 54 thus ensuring the essential lateral stability thereof. As the coil holding part 53 may be turned relative to the rotor 54 when the set screw 62 is released, the zero reading of the transducer 52 may be easily and accurately set.

From the foregoing, it will be apparent that the viscometer just described ensures increased sensitivity with the tube 44 protecting the readout rod 45 contributing as little of the total torsional resistance as is practicable and the means connecting the element that is free to turn relative to the other element providing the necessary lateral stability and as much of the torsional resistance as is practical. By way of example, the tube 44 may be stainless steel tubing having an outside diameter of or in the neighborhood of 0.082 inches and a wall thickness of or in the neighborhood of 0.005 inches, and, as above stated, the diameter of the rod is approximately 0.062 inches.

A viscometer in accordance with another embodiment of the invention is illustrated by FIG. 4 and as many of the parts utilized in that embodiment are or may be the same as those of the viscometer of FIG. 5, corresponding parts are not described and are identified by the suffix addition A to the appropriate reference numerals.

FIG. 4, the outer, open-ended cylinder 28A is fixed on the inner surface of the end wall 13A with diametrically opposed ports 30A adjacent thereto and the inner open-ended cylinder 48A is supported by a torsion unit 10A with its end wall 49A clamped to the part 39A by the nut 51A threaded on its shank 40A. The shaft 18A, however, extends freely through a port 67 in the housing end wall 13A and is supported by a ball bearing unit 68 fixed in the outer end of the port 67 the inner end of which carries a shaft seal 69. A second ball bearing unit 70 is carried by a ring 71 secured to the outer surface of the wall 13A by screws 72. The shaft 18A has an axial bore 73 in which the shank 37A of the first part 36A of the torsion unit 10A is threaded and which is provided with a seal 47A.

The readout rod 45A extends freely through the bore 73 and the readout includes a unit 52A the coil containing part 53A which is fixed on the outer end of the shaft 18A as by the set screw 62A and surrounds the rotor 54A fixed on the readout element 45A. The circuit 55A to the coil 53A includes slip rings 74 and 75 carried by an axial insulator 76 and engaged by bruhes indicated at 77 and 78, respectively.

In this embodiment of the invention, the part 39A of the unit 10A is free to turn, subject to the torsional resistance the unit 10A provides relative to the part 37A which turns with the shaft 18A, rotation of the part 39A opposed by the liquid between the rotating cylinder 48A and the fixed cylinder 28A. The readout provides information on the turning of the cylinder 48A relative to the first part 36A of the torsion unit 10A which rotates with the shaft 18A.

Figure 6:
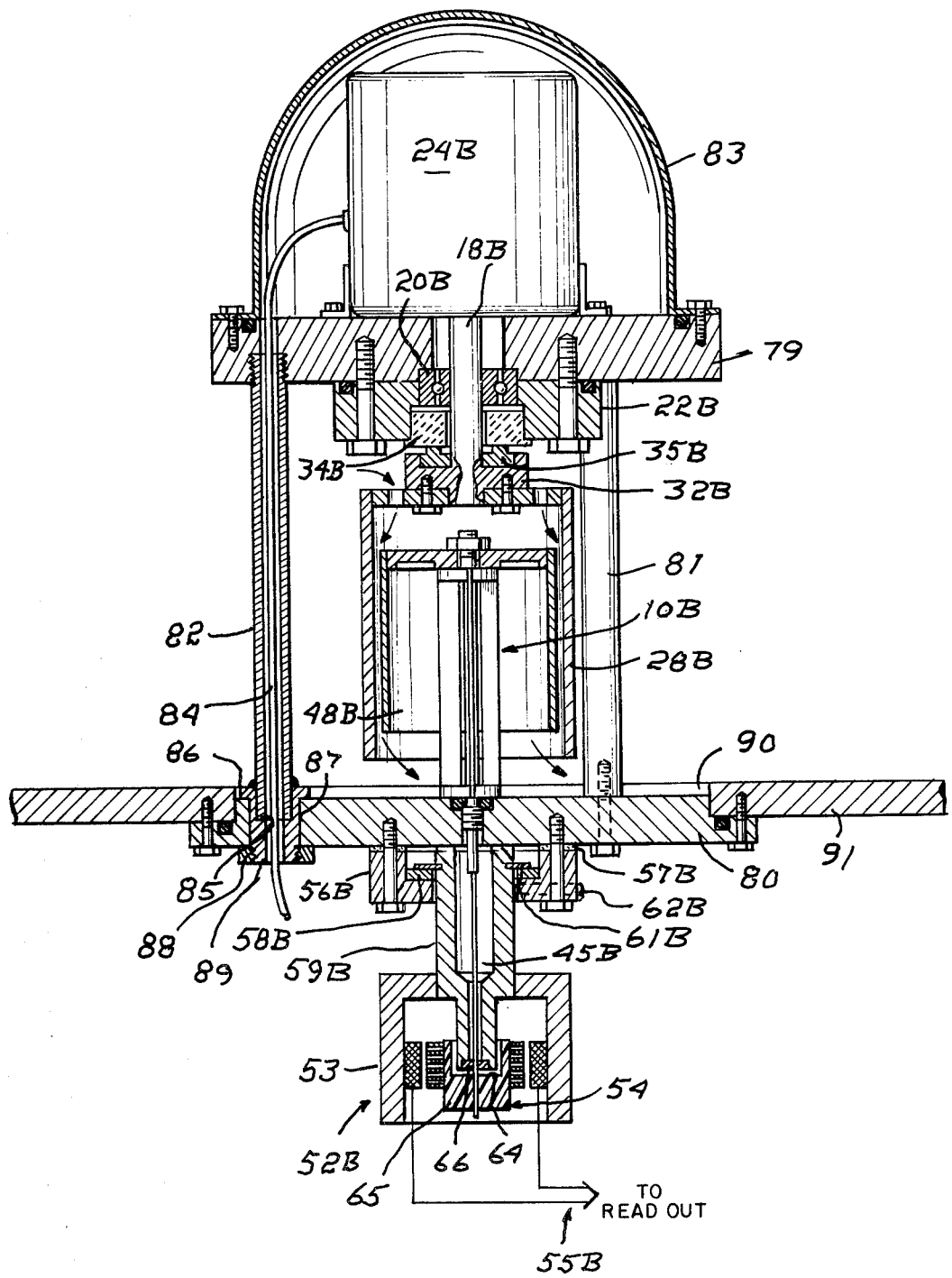
FIG. 6 is a like section through a viscometer similar to that shown in FIG. 5 but with the motor in a chamber sealed from the medium being monitored.

FIG. 6 illustrates yet another viscometer in accordance with the invention and as many of the parts are or may be identical to those of the viscometer illustrated by FIGS. 4 and 5, corresponding parts are identified by the appropriate reference numerals distinguished by the suffix addition B.

The viscometer illustrated by FIG. 6 has a support 79 and an end wall 80 corresponding, respectively to the end walls 12 and 13 of the housing shown in FIG. 5 but interconnected by three posts, two posts 81, only one of which is shown in the drawing, and a tubular post 82. The drive for the shaft 18B is shown as a motor 24B connected directly thereto and mounted on the wall 80 and within a casing 83 sealed thereto. The cord 84, the leads of which are connected to the motor 24B extends through the tubular post 82 which is threaded and sealed in the counterbore of a passage 85 extending through the end wall 80 and through and sealed to a coupling 86 which is sealed to the post 82 and in the counterbored end of a passage 87 extending through the support 79 with a nut 88 threaded on its shank 89. The viscometer of FIG. 6 is for use where it is to be inserted through a port 90 in a chamber wall 91, the wall of a reactor, for example, and secured and sealed thereto.

I claim:

1. A viscometer including a chamber for fluid under pressure, first and second, concentric open ended cylindrical elements within the chamber, one element within the other with a clearance appropriate for the flow of liquid between them, means to rotate one element relative to the other and including a shaft member rotatably entrant of said chamber and connected axially to said one element, a chamber wall member, one of said members having a threaded port extending therethrough and coaxial with said elements and including a supporting portion having an axial passage, torque responsive means to support said inner element and to prevent contact thereof with the outer element, said means including a hub threaded in said port and having an axial passage extending therethrough, a part connected axially to said inner element, means connecting said part to said hub to enable said part to turn relative to said hub, said connecting means including a tube sealed axially to said part and to said hub and means arranged and disposed about said tube to provide lateral stability for said second element and the major percentage of the wanted torsional resistance to the turning thereof, a readout rod within said tube with one end anchored axially of and sealed to the second element and the other end extending freely through the tube and the passage of the supporting portion, the inside diameter of said tube such that the readout rod is close but a free fit therein and the outside diameter of the tube such that the tube provides a minor percentage of said torsional resistance but establishes a wall that is not deformable against the readout rod by the fluid pressure, and a readout device externally of the chamber and including a rotor fixed on the exposed end of the readout rod and a stator surrounding said rotor and fixed on said supporting portion, and a bearing held by the supporting portion, said readout rod extending through and rotatably held by and being unsupported between said bearing and said inner element and said bearing located close to the center of gravity of the rotor.

2. The viscometer of claim 1 in which the tube is stainless steel tubing having an outside diameter of approximately 0.080 inches and a wall thickness of approximately 0.005 inches and the diameter of the readout rod is approximately 0.062 inches.

3. The viscometer of claim 1 in which the part connected to the inner element is a threaded flanged hub and the inner element has an axial threaded seat for said hub.

4. The viscometer of claim 1 in which the threaded port is in the wall member.

5. The viscometer of claim 1 in which the threaded port is in the shaft member.

6. The viscometer of claim 1 in which the stator of the readout device is rotatably held by the supporting portion and releasable means lock said stator thereto.

7. The viscometer of claim 1 in which the supporting portion is an end section of the shaft member.

8. The viscometer of claim 1 in which the supporting portion is a post connected to the wall member.

9. The viscometer of claim 1 in which the rotor has an axial socket dimensioned to receive the outer end of the supporting portion and said bearing within it.

10. The viscometer of claim 1 in which the supporting portion includes a ring fixed on the outer surface of the wall member, a post rotatably held by the fixed ring, and means releasably locking the post to said ring thereby providing means enabling the stator to be turned into and set in a predetermined zero position.

11. The viscometer of claim 10 in which the fixed ring includes an annular flange having a central port in which the post is a close but free fit, a spring washer is seated againt the inner surface of the flange, and a keeper carried by the post is resiliently engaged by the washer and yieldably maintains the post seated against said wall member.

* * * * *